United States Patent [19]
Fisher et al.

[11] Patent Number: 5,947,946
[45] Date of Patent: *Sep. 7, 1999

[54] ABSORBENT ARTICLE HAVING POSITION RETAINING ELEMENT

[75] Inventors: Constance L. Fisher, Cincinnati; Donald C. Roe, West Chester; Carl L. Bergman, Loveland, all of Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/869,362

[22] Filed: Jun. 4, 1997

[51] Int. Cl.$^6$ ....................................................... A61F 13/15
[52] U.S. Cl. .................................. 604/385.1; 604/386
[58] Field of Search ................................ 664/385.1, 386, 664/387

[56] References Cited

U.S. PATENT DOCUMENTS

| | | | |
|---|---|---|---|
| 4,326,528 | 4/1982 | Ryan et al. | |
| 5,154,715 | 10/1992 | Van Iten | 604/387 |
| 5,429,633 | 7/1995 | Davis et al. | 604/387 |

FOREIGN PATENT DOCUMENTS

| | | |
|---|---|---|
| 2121512 | 6/1995 | Canada . |
| 0 335 252 A2 | 10/1989 | European Pat. Off. . |
| 0 712 619 A2 | 5/1996 | European Pat. Off. . |
| WO 96/19165 | 6/1996 | WIPO . |

*Primary Examiner*—Mark O. Polutta
*Attorney, Agent, or Firm*—David M. Weirich; Steven W. Miller; Jacobus C. Rasser

[57] ABSTRACT

A disposable diaper having a first waist region, a second waist region opposed to the first waist region, a crotch region located between the first waist region and the second waist region, a pair of longitudinal edges and a pair of end edges. The disposable diaper further has a topsheet, a backsheet joined with the topsheet, an absorbent core positioned between the topsheet and the backsheet. The diaper includes at least one position retaining element having an initial positioning force and an adjustment force. The position retaining element may be any element included in or joined to the diaper which is bendable and which retains the configuration, orientation, angle, and/or shape of its deformed state until a repositioning force is applied. The position retaining element may be operatively associated with any element(s) of the diaper including the topsheet, backsheet, core, leg cuffs, side panels, waist feature or fastening system.

20 Claims, 5 Drawing Sheets

ABSORBENT ARTICLE HAVING POSITION RETAINING ELEMENT

BACKGROUND OF THE INVENTION

The major function of absorbent articles such as disposable diapers and incontinence briefs or undergarments is to absorb and contain body exudates. In order to work effectively, such absorbent articles must maintain a good fit about the wearer throughout the time of use. Further, to be cost effective the articles must be capable of providing proper fit to a large range of wearer sizes and shapes.

In conventional diapers and other disposable absorbent articles, sustained fit is often provided by a combination of fastening systems, elastics and the shape of the article. Although many of the elements of conventional disposable absorbent articles, such as side panels, ears, or chasses are bendable and positionable (some via wearer or caregiver action, others via pre-stretched elastic contraction effects), the bendable elements are unable to retain the position, or geometry to which they have been conformed once the original bending or deformation force has been removed. The diaperer also has a difficult task fitting the diaper to the wearer because the different elements of the diaper must be positioned and held in place while the diaper is fastened. Further, the fastening system of the diaper is often stiff and less conformable than other portions of the diaper. Accordingly, the fastening system may actually provide forces which negatively affect the fit of the diaper. Thus, even if a good fit is obtained when the diaper is fitted to the wearer, it often loosens or somehow degrades shortly thereafter. Accordingly, it would be desirable to provide an absorbent article with position retaining bendable elements which have the ability to maintain the geometry achieved by the bending and deformation forces applied by the diaperer.

Therefore, it is an object of the present invention to provide position retaining bendable side panels or ears for disposable absorbent articles.

It is a further object of the present invention is to provide position retaining bendable chassis elements for disposable absorbent articles.

It is yet another object of the present invention is to provide position retaining bendable leg cuff elements for disposable absorbent articles.

Another object of the present invention is to provide position-retaining bendable fastening elements.

Yet another object of the present invention is to provide position retaining bendable waist elements for disposable absorbent articles.

SUMMARY OF THE INVENTION

The present invention is directed to a disposable absorbent article having a first waist region, a second waist region opposed to the first waist region, a crotch region located between the first waist region and the second waist region, a pair of longitudinal edges and a pair of end edges. The disposable absorbent article further comprises a topsheet, a backsheet joined with the topsheet, an absorbent core positioned between the topsheet and the backsheet. The absorbent core includes a pair of side edges and a pair of waist edges. The diaper includes a position retaining element having an initial positioning force and an adjustment force. The position retaining element may be operatively associated with any element(s) of the diaper including the topsheet, backsheet, core, leg cuffs, side panels, waist feature or fastening system.

BRIEF DESCRIPTION OF THE DRAWINGS

While the specification concludes with claims particularly pointing out and distinctly claiming the subject matter which is regarded as the present invention, it is believed that the invention will be better understood from the following drawings, in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to an absorbent article which is formed of separate parts united together to form a coordinated entity so that it does not require separate manipulative parts like a separate holder and liner. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like. A preferred embodiment of an absorbent article of the present invention is the unitary disposable absorbent article, diaper 20, shown in FIG. 1.

Figure 1:
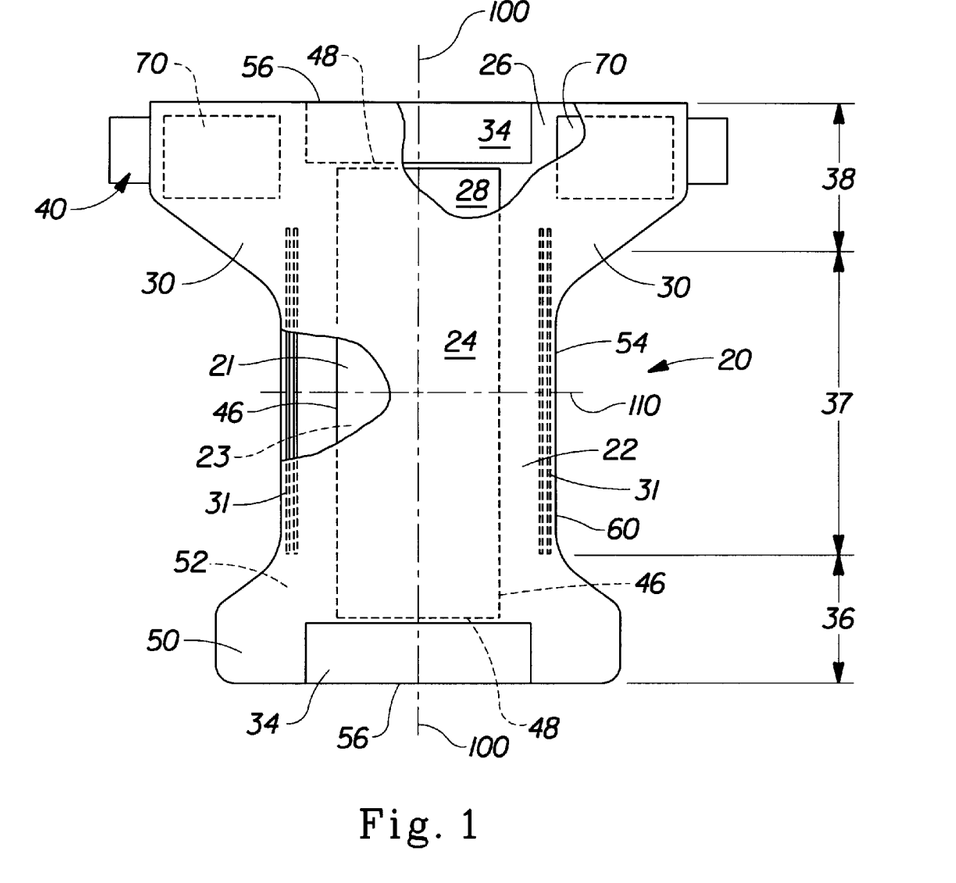
FIG. 1 is a plan view of an embodiment of a diaper of the present invention in its flat-out, uncontracted state (i.e., with elastic induced contraction pulled out) showing the construction of the diaper.

FIG. 1 is a plan view of one preferred embodiment of the diaper 20 of the present invention in its flat-out, uncontracted state (i.e., with elastic induced contraction pulled out) with portions of the structure being cut-away to more clearly show the construction of the diaper 20. The portion of the diaper 20 which faces or contacts the wearer, the inner surface 50, is oriented towards the viewer. As shown in FIG. 1, the diaper 20 preferably comprises a liquid pervious topsheet 24; a liquid impervious backsheet 26 joined with the topsheet 24; an absorbent core 28 positioned between the topsheet 24 and the backsheet 26; elasticized side panels 30; elasticized leg cuffs 32; and a waist feature 34. (As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.) The diaper 20 is shown in FIG. 1 to have an outer surface 52, an inner surface 50 opposed to the outer surface 52, first waist region 36, a second waist region 38 opposed to the first waist region 36, a crotch region 37 positioned between the first waist region 36 and the second waist region 38, and a periphery 60 which is defined by the outer edges of the diaper 20 in which the longitudinal edges are designated 54 and the end edges are designated 56. The inner surface 50 of the diaper 20 generally comprises that portion of the diaper 20 which is positioned adjacent to the wearer's body during use (i.e., the inner surface 50 generally is formed by at least a portion of the topsheet 24 and other components joined to the topsheet 24). The outer surface 52 generally comprises that portion of the diaper 20 which is positioned away from the wearer's body (i.e., the outer surface 52 generally is formed by at least a portion of the backsheet 26 and other components joined to the backsheet 26). The diaper 20 also has a longitudinal centerline 100 and a lateral centerline 110.

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 60 of the diaper 20. While the topsheet 24, the backsheet 26, and the absorbent core 28 may include many different materials and may be assembled in a variety of well known configurations, preferred diaper materials and configurations are described generally in U.S. Pat. No. 3,860,003 entitled "Contractable Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on June 22, 1993; each of which is incorporated herein by reference.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface 23, a body surface 21, side edges 46, and waist edges 48. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent material include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The backsheet 26 is preferably impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26. In one embodiment, the backsheet 26 may comprise a structural elastic-like film (SELF) web. SELF webs suitable for the present invention are more completely described in the commonly assigned U.S. Pat. No. 5,518,801 entitled "Web Materials Exhibiting Elastic-Like Behavior" issued to Chappell et al. on May 21, 1996, which is incorporated herein by reference.

The topsheet 24 is preferably compliant, soft feeling, and non-irritating to the wearer's skin. Further, the topsheet 24 is preferably liquid pervious, permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28. There are a number of manufacturing techniques which may be used to manufacture the topsheet 24. For example, the topsheet 24 may be a nonwoven web of fibers spunbond, carded, wet-laid, meltblown, hydroentangled, combinations of the above, or the like. One preferred topsheet is carded and thermally bonded by means well known to those skilled in the fabrics art. The topsheet may comprise a web of staple length polypropylene fibers such as P-8 manufactured by Veratec, Inc., a Division of International Paper Company, of Walpole, Mass. Another preferred topsheet includes formed films as described in U.S. Pat. No. 3,929,135, issued to Thompson on Dec. 30, 1975; U.S. Pat. No. 4,324,246 issued to Mullane et al. on Apr. 13, 1982; U.S. Pat. No. 4,342,3145 issued to Radel et al on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are hereby incorporated by reference herein.

The diaper 20 preferably further comprises elasticized leg cuffs 32 to improve containment of liquids and other body exudates. Each elasticized leg cuff may include several different embodiments for reducing the leakage of body exudates in the leg regions. (The leg cuff can also be referred to as leg bands, side flaps, barrier cuffs, or elastic cuffs.) U.S.

Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs 32) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff 31 and a barrier cuff 32.

The diaper 20 preferably also includes a waist feature 34 that helps provide improved fit and containment. The waist feature 34 is that portion or zone of the diaper 20 which is intended to elastically expand and contract to dynamically fit the wearer's waist. The elastic waist feature 34 generally extends longitudinally outwardly from at least one of the waist edges 48 of the absorbent core 28 and generally forms at least a portion of the end edge 56 of the diaper 20. Although disposable diapers are generally constructed so as to have two elastic waist features, one positioned in the first waist region 36 and one positioned in the second waist region 38, diapers can be constructed with a single elastic waist feature. Further, while the elastic waist feature 34 or any of its constituent elements can include a separate element affixed to the diaper 20, the elastic waist feature 34 is preferably constructed as an extension of other elements of the diaper 20 such as the backsheet 26, the topsheet 24 or both the backsheet 26 and the topsheet 24. Examples of suitable waist features include those described in U.S. Pat. No. 4,515,595 issued to Kievit et al. on May 7, 1985 and the above referenced U.S. Pat. No 5,151,092 issued to Buell on Sep. 9, 1992; and U.S. Pat. No. 5,221,274 issued to Buell on Jun. 22, 1993; each of which is incorporated herein by reference.

The diaper 20 may also include a fastening system 40 which helps to maintain lateral tension around the circumference of the diaper in order to keep the diaper in place about the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; the hereinbefore referenced U.S. Pat. No. 5,151,092 issued to Buell on Sep. 9, 1992; and U.S. Pat. No. 5,221,274 issued to Buell on Jun. 22, 1993; each of which is incorporated herein by reference.

The disposable absorbent article of the present invention further includes one or more position retaining elements 70. As used herein, the term "position retaining element" refers to any element included in or joined to the diaper 20 which is bendable and which retains the configuration, orientation, angle, and/or shape of its deformed state until a repositioning force is applied. For example, if the position retaining element is bent to an angle at 90 degrees from its original position, it will substantially retain the new angle of 90 degrees until a force is applied which reconfigures the element. Thus, the position retaining element 70 has the ability to deform to a particular geometry or configuration as a result of an initial positioning force as well as the ability to retain that position without the need to maintain the initial positioning forces or any additional forces on the position retaining element 70. Further, the position retaining element 70 should be able to maintain its geometry or its configuration even if subsequent forces are applied which tend to further deform the position retaining element 70, unless the forces are greater than a specified amount. Repositioning or adjustment forces are typically desired to be of about the same magnitude as the initial positioning force.

In preferred embodiments, the initial positioning forces needed to configure the position retaining element 70 as desired fall within a certain range for disposable diapers to be fitted to babies. (Of course, the exact range can vary according to the specific needs of the size, age and weight of the intended users.) Generally, the initial positioning force and subsequent adjustment force required to bend the element are greater than the forces (e.g., gravity, elastic contraction, etc.) that would act to return the element toward its original shape (i.e., away form the caregiver-defined orientation). On the other hand, the initial positioning force and subsequent adjustment force of the position retaining element 70 must be low enough that the desired bending is readily accomplished by the caregiver. Typically, the initial positioning force is at least about 25 grams and less than about 1000 grams and preferably at least about 50 grams and less than about 1000 grams. The repositioning force is preferably greater than about 25 grams and preferably between about 50 grams and about 1000 grams. More preferably, the initial positioning force is between about 50 grams and about 600 grams and the repositioning force is between about 50 grams and about 600 grams.

Disposable absorbent articles such as adult incontinence devices may require different ranges of positioning forces in order to be effective. For example, an adult incontinence device may require an initial positioning force between about 50 grams and about 1000 grams and a repositioning force between about 100 grams and about 600 grams.

The positioning and adjustment forces can be measured according to the following procedure. The portion of the diaper 20 including the position retaining element 70 is identified and placed on a flat surface and clamped or affixed thereto along the intended bending line. The portion of the diaper 20 including the position retaining element 70 is then folded upward, away from the surface until it is extending away from the surface at an angle of 90 degrees. It may be necessary to hold the portion of the diaper 20 to be folded along the line of bending to ensure that the position retaining element 70 is bent as desired. The force needed to fold the position retaining element to the 90 degree position is the initial positioning force. A standard extensible force gauge is used to measure the positioning force. After a period of 5 minutes, an adjustment force is applied to the portion of the diaper 20 which was folded to the 90 degree position. The adjustment force is measured as the force needed to move the folded portion of the diaper 45 degrees from the 90 degree position. This test is run at standard temperature, atmospheric pressure and relative humidity (70° F., 1 atm pressure and 50% relative humidity).

The position retaining element 70 may be embodied throughout the diaper 20 or in specific areas such as the side panels 30, the cuffs 31 and 32, the absorbent core 28 or the waist feature(s) 34. Further, the position retaining element 70 may be a separate element incorporated in a specific portion of the product or may include a portion of one or more of the diaper 20 elements such as the topsheet 24, the backsheet 26 and/or the core 28. In one preferred embodiment, as shown in FIG. 1, the position retaining element 70 is disposed in at least one of the side panels 30 which are located in the second waist region 38. (As used herein, the term "disposed" is used to mean that an element (s) of the diaper is formed (joined and positioned) in a particular place or position as a unitary structure with other elements of the diaper or as a separate element joined to another element of the diaper.)

In other preferred embodiments, the position retaining element 70 is disposed in at least a portion of the chassis 22 of the diaper 20. (As used herein, the term "chassis" refers to the portion of the diaper 20 which is intended to receive and contain exudates. Generally, the chassis 22 includes the topsheet 24, the backsheet 26 and the absorbent core 28. Elements such as side panels 30, and barrier leg cuffs are often joined to the chassis 22, however, embodiments are contemplated wherein the chassis 22 includes such features as side panels and leg cuffs.) Position retaining elements 70 disposed in the chassis 22 allow the chassis 22 to be molded by the caregiver to the wearer's individual body geometry. The position retaining element(s) 70 may include one or more individual elements which can act separately or which may be operatively associated with each other. Further, the position retaining element(s) 70 may be disposed in a direction parallel to either the lateral centerline 110 or the longitudinal centerline 100, or at any angle to either centerline.

The position retaining element 70 may be of any shape and may include any number of separate or unitary elements. Some nonlimiting examples of suitable position retaining elements include ductile wires, coated wires, metallic foils, rods, shafts, beams, loops, mesh, screens, films, foams, adhesives, woven or nonwoven webs and the like, or any combinations thereof. The position retaining elements 70 may comprise plastics, metals such as copper, aluminum, lead or steel; organic materials like waxes, clays; or any other mixture of these or other materials.

Figure 2:
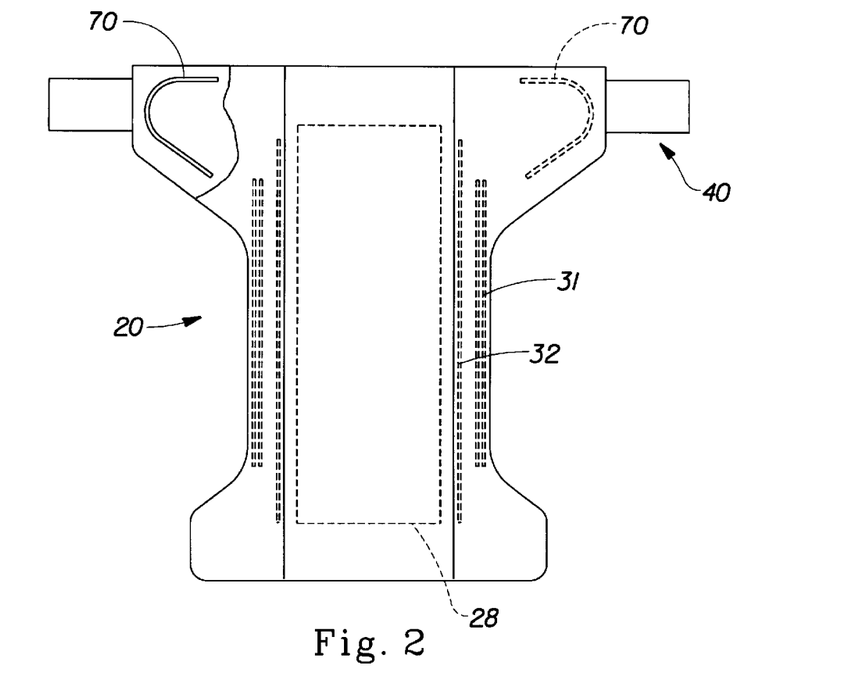
FIG. 2 is a plan view of another embodiment of a diaper of the present invention in its flat-out, uncontracted state having position retaining elements disposed in each side panel of the diaper.
Figure 3:
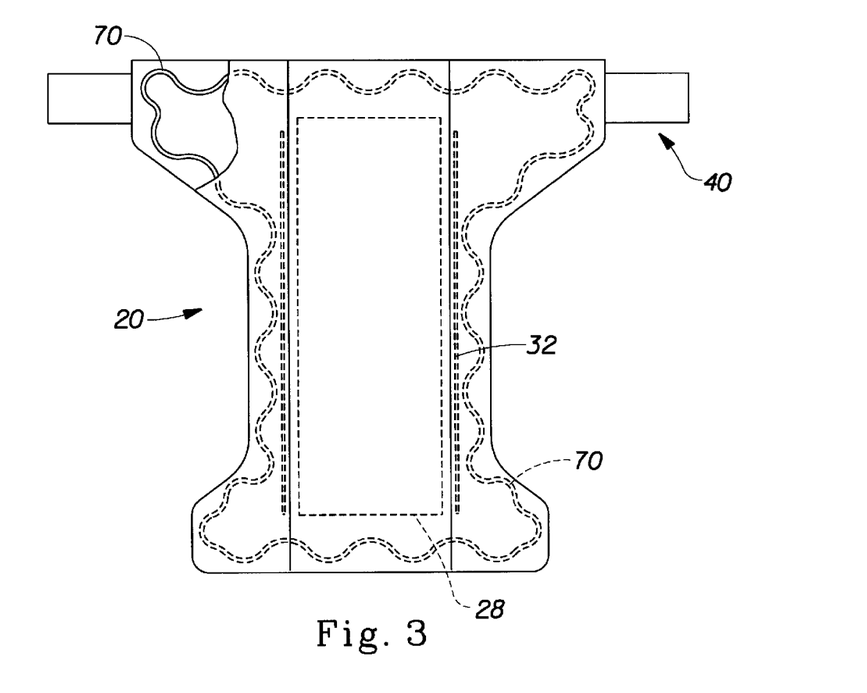
FIG. 3 is a plan view of another embodiment of a diaper of the present invention in its flat-out, uncontracted state having a position retaining element disposed throughout a chassis of the diaper.

As shown in FIGS. 2–7, the position retaining element 70 may be located in any portion of the diaper 20. For example, FIG. 2 shows a position retaining element 70 disposed in portions of each side panel 30. The position retaining element 70 is shown as a strand of material which is located between the topsheet 24 and backsheet 26 around the perimeter of each side panel 30, approximately 1 cm from the edge. FIG. 3 shows a position retaining element 70 disposed throughout the chassis 22 of diaper 20. The position retaining element 70 may be in the shape of a wave (approximately 1.5 cm amplitude and 1 cm peak-to-peak distance) located between the topsheet 24 and backsheet 26 along the longitudinal edges 54 and end edges 56 of the diaper 20. In embodiments such as those shown in FIGS. 1–3, the diaper 20 may be fitted to the wearer without the need for a fastening system. Rather, the position retaining element 70 allows the diaper 20 to be shaped as desired and then maintains the shape throughout the time of use.

Figure 4:
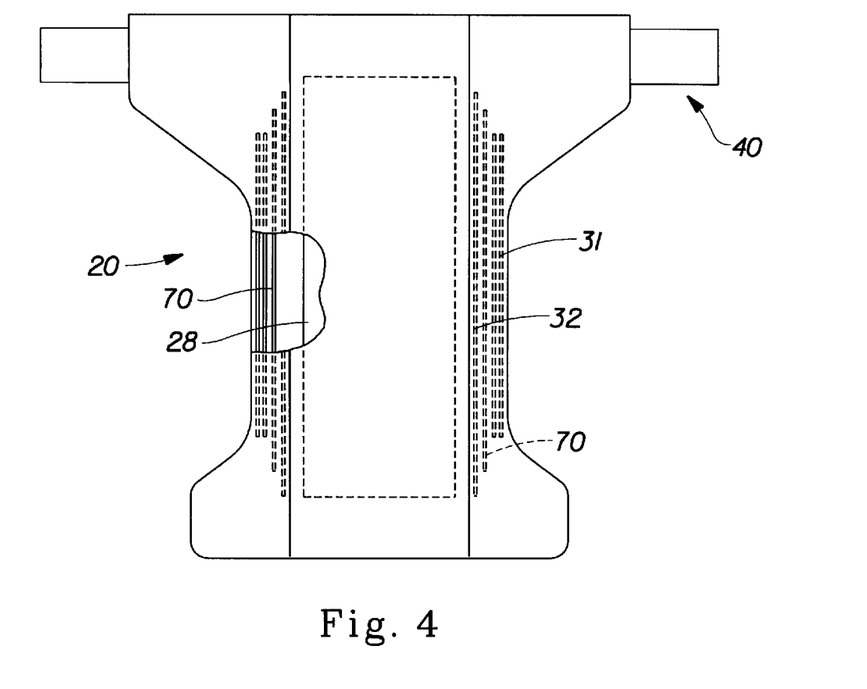
FIG. 4 is a plan view of another embodiment of a diaper of the present invention in its flat-out, uncontracted state having position retaining elements located adjacent a core in a crotch region of the diaper.
Figure 5:
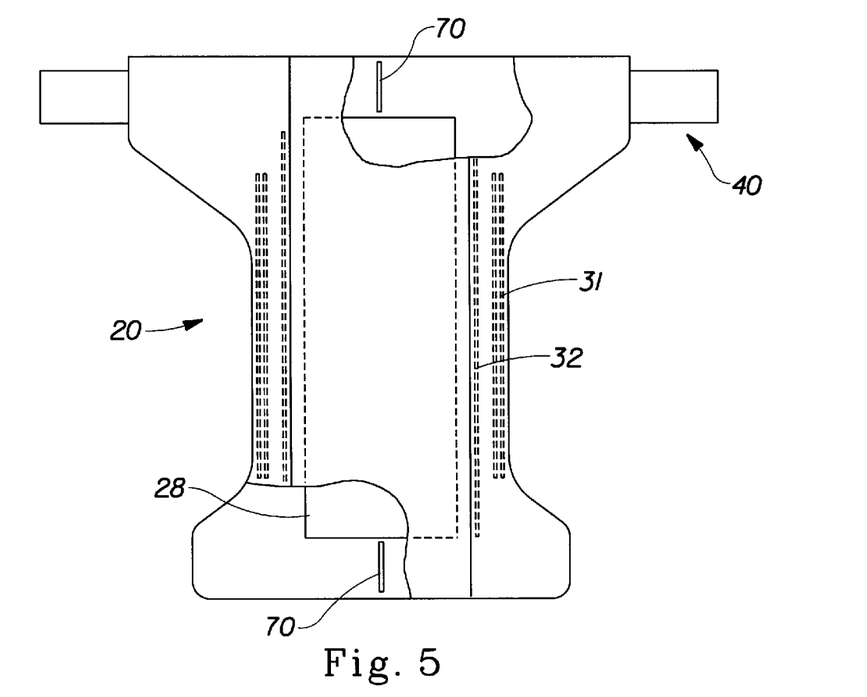
FIG. 5 is a plan view of another embodiment of a diaper of the present invention in its flat-out, uncontracted state having position retaining elements located in both waist regions of the diaper.
Figure 6:
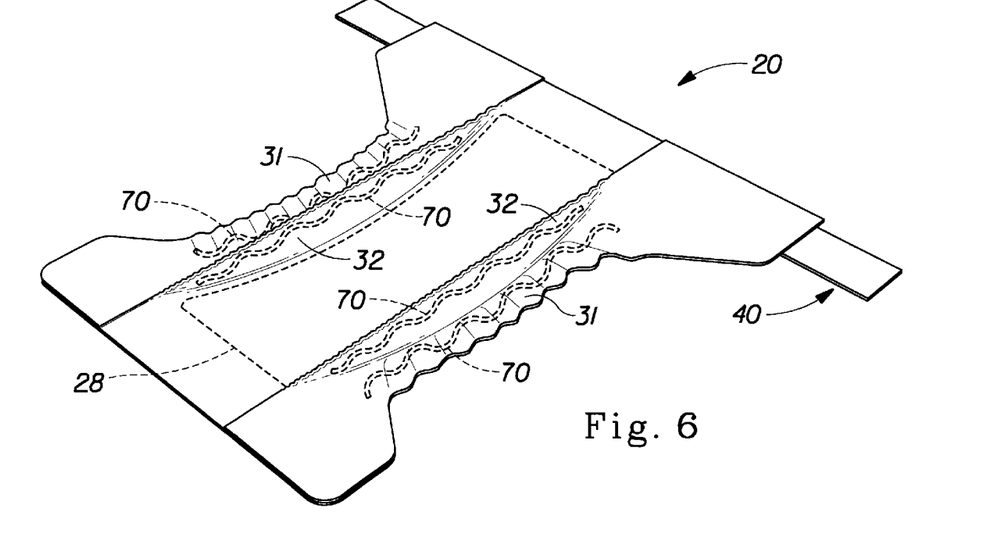
FIG. 6 is a perspective view of another embodiment of a diaper of the present invention in its flat-out, uncontracted state having position retaining elements in both barrier leg cuffs and gasketing leg cuffs of the diaper.
Figure 7:
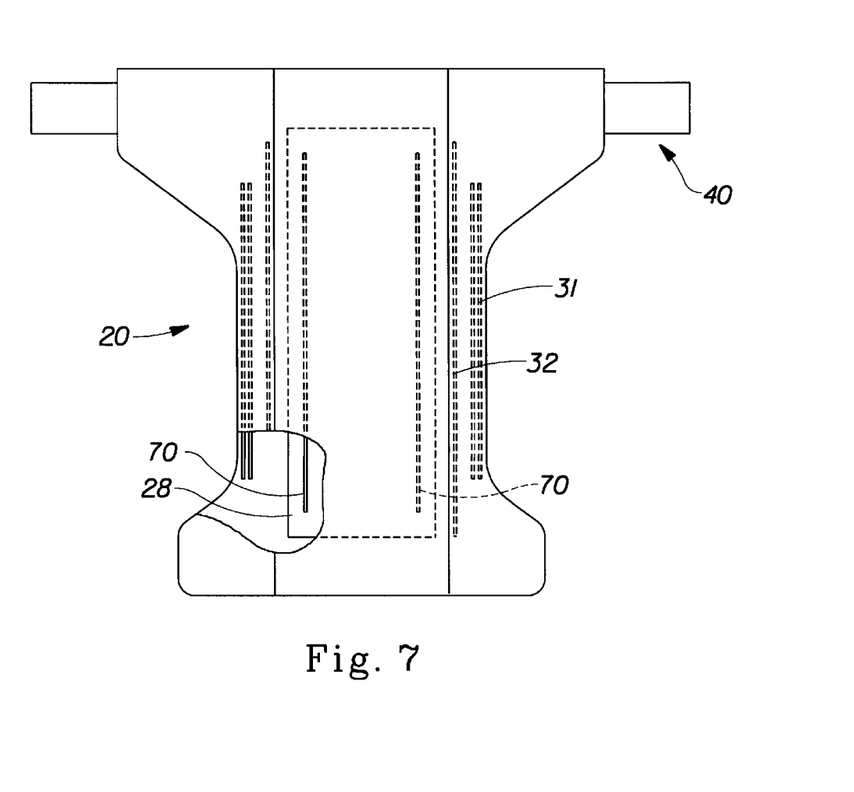
FIG. 7 is a plan view of another embodiment of a diaper of the present invention in its flat-out, uncontracted state having position retaining elements adjacent each side edge of a core of the diaper.

FIGS. 4 and 5 show position retaining elements 70 located adjacent the core 28 in the crotch region 37 and the first and second waist regions 36 and 38, respectively. FIG. 6 shows position retaining elements in the barrier leg cuffs 32 and the gasketing leg cuffs 33. FIG. 7 shows a position retaining element 70 adjacent each side edge 46 of the core 28. In such embodiments, the position retaining element 70 may be operatively associated with the topsheet 24, the absorbent core 28 or both the topsheet 24 and the core 28. Thus, the topsheet 24 and/or core 28 may be shaped as desired by the diaperer to improve the fit and containment of the diaper 20. Thus, the topsheet 24 may be shaped so as to provide contact with the wearer's skin in some areas while not in other areas or may be shaped to include a pocket or pockets for receiving and storing exudates.

Figure 8:
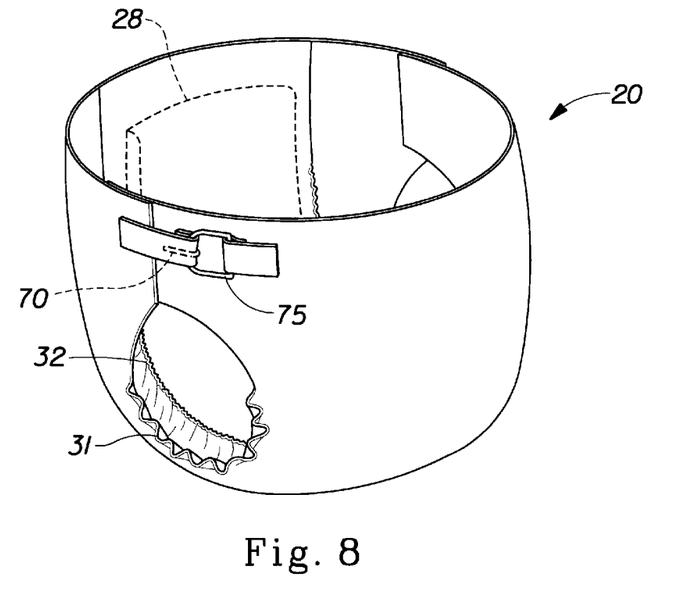
FIG. 8 is a perspective view of another embodiment of a diaper of the present invention when its fastened position having a position retaining element located in a fastening system of the diaper.
Figure 9:
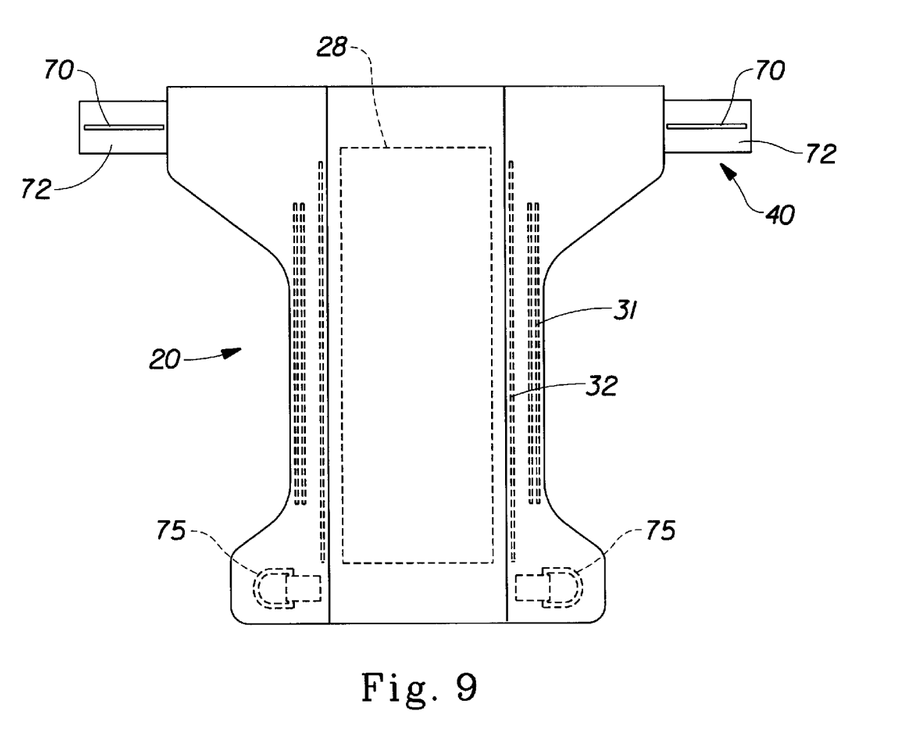
FIG. 9 is a plan view of the embodiment of FIG. 8 in its flat-out, uncontracted state.

The position retaining element 70 of the present invention may also be included in the fastening system 40, as shown in FIGS. 8 and 9. For example, the diaper 20 may include a position retaining fastening system 40 which acts as a primary or secondary fastener for the diaper. (A "primary fastener" is a fastener used by itself or in conjunction with other primary fasteners to provide means by which the diaper is secured about the wearer. A "secondary fastener" is a fastener used in conjunction with the primary fastening means to provide the diaper with a better fit about the wearer or to provide additional fastening features such as a disposal feature.)

As shown in FIGS. 8 and 9, the fastening system 40 may include a loop portion 75 and a tab portion 72. The tab portion 72 preferably includes at least one position retaining element 70. The position retaining element 70 is preferably bendable such that the diaperer can bend the tab portion 72 about the loop portion 75. The tab portion may be bent either toward or away from the outer surface of the diaper 20. In the configuration shown in FIG. 8, the loop portion 75 and the tab portion 72 act as the primary fastener to hold the diaper 20 on the wearer. The position retaining element 70 provides the tab portion 72 with the ability to maintain its shape about the loop portion 75 throughout the time the diaper is worn. Further, the position retaining element 70 of the tab portion 72 allows the tab portion 72 to be opened or reconfigured if desired. Thus, the present invention provides a refastenable fastening system which can be opened, closed or adjusted several times without reducing its overall effectiveness. The loop portion 75 may be any loop of material joined with or integral with the diaper 20. The loop portion 75 should be strong enough to hold the diaper 20 in a fastened configuration throughout normal usage periods when normal dynamic forces are applied to the diaper. Preferably the tab portion 72 has a positioning force of between greater than 25 grams, preferably between about 50 grams and about 1000 grams. The adjustment force of the position retaining element is also preferably greater than 25 grams and preferably between about 50 grams and about 1000 grams.

The diaper 20 of the present invention, as shown in FIG. 1, is preferably applied to a wearer by positioning one of the waist regions, preferably the second waist region 38, under the wearer's back and drawing the remainder of the diaper 20 between the wearer's legs. The other waist region, preferably the first waist region 36, is positioned across the front of the wearer. The diaperer then applies an initial positioning force to deform the position retaining element 70 such that the diaper fits properly around the wearer. The diaperer may readjust the position retaining element 70 as necessary to improve the fit of the diaper 20. Once the diaper is in the desired configuration, the diapering operation is complete. However, the diaperer may wish to implement an additional fastening system (either unitary with the diaper, such tapes or hook and loop fasteners, or separate fasteners like pins) to ensure that the diaper is maintained in the proper configuration in the event the wearer is capable of deforming the position retaining element while wearing the diaper 20. If the diaper 20 includes the tab and loop fastening system 40, as described above, the diaperer will bend the tab portion 72 of the fastening system 40 about the loop 75. (One example is shown in FIG. 8) The fastening system may be opened by simply bending the tab portion 72 to allow it to slip out of the loop portion 75. The fastening system 40 may also be refastened or adjusted by bending the tab portion 72 about the loop portion in any desired configuration.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper having a first waist region, a second waist region opposed to said first waist region and a crotch region located between said first waist region and said second waist region, a pair of longitudinal edges and a pair of end edges, said first waist region and said second waist region of the disposable diaper encircling at least a portion of the waist of a wearer when the disposable diaper is worn, the disposable diaper comprising:
    a topsheet;
    a backsheet joined with said topsheet;
    an absorbent core positioned between said topsheet and said backsheet, said absorbent core including a pair of side edges and a pair of waist edges; and
    a side panel disposed in said first waist region and extending laterally outwardly from at least one of said side edges of said absorbent core to encircle at least a portion of the wearer's waist when worn, said side panel including a position retaining element having an initial positioning force of greater than about 25 grams and an adjustment force of greater than about 25 grams.

2. The disposable diaper of claim 1 further comprising a fastener disposed on said side panel for joining said first waist region and said second waist region.

3. A disposable diaper having a first waist region, a second waist region opposed to said first waist region and a crotch region located between said first waist region and said second waist region, a pair of longitudinal edges and a pair of end edges, said first waist region and said second waist region of the disposable diaper encircling at least a portion of the waist of a wearer when the disposable diaper is worn, the disposable diaper comprising:
    a topsheet;
    a backsheet joined with said topsheet;
    an absorbent core positioned between said topsheet and said backsheet, said absorbent core including a pair of side edges and a pair of waist edges; and
    a waist feature disposed in said first waist region including a position retaining element having an initial positioning force of greater than about 25 grams and an adjustment force of greater than about 25 grams.

4. A disposable diaper having a first waist region, a second waist region opposed to said first waist region and a crotch region located between said first waist region and said second waist region, a pair of longitudinal edges and a pair of end edges, said first waist region and said second waist region of the disposable diaper encircling at least a portion of the waist of a wearer when the disposable diaper is worn, the disposable diaper comprising:
    a topsheet;
    a backsheet joined with said topsheet;
    an absorbent core positioned between said topsheet and said backsheet, said absorbent core including a pair of side edges and a pair of waist edges;
    a side panel disposed in said first waist region and extending laterally outwardly from at least one of said side edges of said absorbent core to encircle at least a portion of the wearer's waist when worn; and
    a gasketing leg cuff adjacent each said longitudinal edge, wherein each said gasketing leg cuff includes a position retaining element having an initial positioning force of greater than about 25 grams and an adjustment force of greater than about 25 grams.

5. A disposable diaper having a first waist region, a second waist region opposed to said first waist region and a crotch region located between said first waist region and said second waist region, a pair of longitudinal edges and a pair of end edges, said first waist region and said second waist region of the disposable diaper encircling at least a portion of the waist of a wearer when the disposable diaper is worn, the disposable diaper comprising:
    a topsheet;
    a backsheet joined with said topsheet;
    an absorbent core positioned between said topsheet and said backsheet, said absorbent core including a pair of side edges and a pair of waist edges; and
    said topsheet operatively associated with a position retaining element having an initial positioning force of greater than about 25 grams and an adjustment force of greater than about 25 grams.

6. A disposable diaper having a first waist region, a second waist region opposed to said first waist region and a crotch region located between said first waist region and said second waist region, a pair of longitudinal edges and a pair of end edges, said first waist region and said second waist region of the disposable diaper encircling at least a portion of the waist of a wearer when the disposable diaper is worn, the disposable diaper comprising:
    a topsheet;
    a backsheet joined with said topsheet;
    an absorbent core positioned between said topsheet and said backsheet, said absorbent core including a pair of side edges and a pair of waist edges; and
    a barrier leg cuff including a position retaining element having an initial positioning force of greater than about 25 grams and an adjustment force of greater than about 25 grams.

7. A disposable diaper having a first waist region, a second waist region opposed to said first waist region and a crotch region located between said first waist region and said second waist region, a pair of longitudinal edges and a pair of end edges, said first waist region and said second waist region of the disposable diaper encircling at least a portion of the waist of a wearer when the disposable diaper is worn, the disposable diaper comprising:
    a topsheet;
    a backsheet joined with said topsheet;
    an absorbent core positioned between said topsheet and said backsheet, said absorbent core including a pair of side edges and a pair of waist edges; and
    said absorbent core including a position retaining element having an initial positioning force of greater than about 25 grams and an adjustment force of greater than about 25 grams.

8. The disposable diaper of claims 1, 3, 5, 6 or 7 wherein said position retaining element has an initial positioning force of between about 50 grams and about 1000 grams and an adjustment force of between about 50 grams and about 1000 grams.

9. The disposable diaper of claim 1, 3, 5, 6 or 7 wherein said position retaining element has an initial positioning force of between about 50 grams and about 600 grams and an adjustment force of between about 50 grams and about 600 grams.

10. The disposable diaper of claims 1, 3, 5, 6 or 7 wherein the position retaining element is chosen from the group consisting of: copper wire, plastic, foam, clay, scrim, wax, foil, adhesive, woven webs and nonwoven webs.

11. A disposable diaper having a first waist region, a second waist region opposed to said first waist region, a crotch region located between said first waist region and said second waist region, a first longitudinal edge and a second longitudinal edge, the disposable diaper comprising:
- a topsheet;
- a backsheet joined with said topsheet;
- an absorbent core positioned between said topsheet and said backsheet, said absorbent core including a pair of side edges and a pair of waist edges; and
- a fastening system for joining said first waist region and said second waist region, said fastening system including:
  - a tab portion adjacent said first longitudinal edge in said second waist region, said tab portion including at least one position retaining element;
  - a loop portion adjacent said first longitudinal edge in said first waist region; and
  - said tab portion being bendable about said loop portion with an initial positioning force of greater than about 25 grams.

12. The disposable diaper of claim 11 wherein said position retaining element is chosen from the group consisting of: copper wire, plastic, foam, clay, scrim, wax, foil, adhesive, woven webs and nonwoven webs.

13. The disposable diaper of claim 11 wherein said position retaining element has an adjustment force of greater than about 25 grams.

14. The disposable diaper of claim 11 wherein said positioning element has an initial positioning force of between about 25 grams and about 1000 grams and an adjustment force of between about 25 grams and about 1000 grams.

15. A disposable diaper having a first waist region, a second waist region opposed to said first waist region and a crotch region located between said first waist region and said second waist region, a pair of longitudinal edges and a pair of end edges, said first waist region and said second waist region of the disposable diaper encircling at least a portion of the waist of a wearer when the disposable diaper is worn, the disposable diaper comprising:
- a topsheet;
- a backsheet joined with said topsheet;
- an absorbent core positioned between said topsheet and said backsheet, said absorbent core including a pair of side edges and a pair of waist edges; and
- a position retaining element disposed between said topsheet and said backsheet along at least a portion of at least one of said of pair of longitudinal edges and at least a portion of at least one of said of pair of end edges of the diaper, said position retaining element having an initial positioning force of greater than about 25 grams and an adjustment force of greater than about 25 grams.

16. The disposable diaper of claim 15 wherein said position retaining element is disposed along at least a portion of each of said pair of longitudinal edges and at least a portion of one of said pair of end edges of the diaper.

17. The disposable diaper of claim 15 wherein said position retaining element is disposed along at least a portion of one of said pair of longitudinal edges and at least a portion of each of said of pair of end edges of the diaper.

18. The disposable diaper of claim 15 wherein said position retaining element is disposed along at least a portion of each of said of pair of longitudinal edges and at least a portion of each of said of pair of end edges of the diaper.

19. The disposable diaper of claim 18 further comprising a side panel disposed in said first waist region and extending laterally outwardly from at least one of said side edges of said absorbent core to encircle at least a portion of the wearer's waist when worn, wherein said position retaining element extends into said side panel.

20. The disposable diaper of claim 15 wherein said position retaining element is chosen from the group consisting of: copper wire, plastic, foam, clay, scrim, wax, foil, adhesive, woven webs and nonwoven webs.

* * * * *